(12) United States Patent
Dubois et al.

(10) Patent No.: US 6,684,701 B2
(45) Date of Patent: Feb. 3, 2004

(54) SYSTEM AND METHOD OF DETERMINING POROSITY IN COMPOSITE MATERIALS USING ULTRASOUND

(75) Inventors: Marc Dubois, Clifton Park, NY (US); John B. Deaton, Jr., Niskayuna, NY (US); Peter W. Lorraine, Niskayuna, NY (US); Thomas E. Drake, Jr., Fort Worth, TX (US); Robert J. Filkins, Fonda, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 09/905,444

(22) Filed: Jul. 13, 2001

(65) Prior Publication Data

US 2002/0066318 A1 Jun. 6, 2002

Related U.S. Application Data

(60) Provisional application No. 60/218,341, filed on Jul. 14, 2000.

(51) Int. Cl.[7] .............................................. G01H 1/00
(52) U.S. Cl. ....................................................... 73/579
(58) Field of Search .......................... 73/579, 599, 600, 73/620, 627

(56) References Cited

U.S. PATENT DOCUMENTS

| 4,006,625 A | 2/1977 | Davis .......................... 73/71.4 |
| 4,089,225 A | 5/1978 | Kraska et al. ................. 73/614 |
| 4,283,953 A | 8/1981 | Plona ........................... 73/589 |
| 4,426,155 A | 1/1984 | Monchalin ................... 356/346 |

(List continued on next page.)

FOREIGN PATENT DOCUMENTS

| EP | 0092191 A2 | 10/1983 |
| EP | 0123427 A2 | 3/1986 |
| EP | 0374262 A1 | 6/1990 |
| EP | 0605409 A2 | 6/1992 |
| EP | 0636881 A1 | 2/1995 |
| EP | 0599863 A1 | 8/1995 |
| EP | 0809107 A1 | 7/1997 |
| EP | 1112493 A2 | 3/2000 |

OTHER PUBLICATIONS

PCT International Search Report.
WO 98 22814; John W. Dixon, et al.; Method and System for Processing Measurement Signals to Obtain a Value for a Physical Parameter.

(List continued on next page.)

*Primary Examiner*—Richard A. Moller
(74) *Attorney, Agent, or Firm*—Koestner Bertani, LLP (57) ABSTRACT

The invention provides for ultrasonically measuring the porosity in a sample composite material by accessing only one side of the sample composite material and includes the steps of measuring a sample ultrasonic signal from the sample composite material, normalizing the sample ultrasonic signal relative to the surface echo of the sample composite material, and isolating a sample back-wall echo signal from the sample ultrasonic signal. A sample frequency spectrum of the sample back-wall ultrasonic signal is then determined. Next, the method and system include the steps of measuring a reference ultrasonic signal from a reference composite material, normalizing the reference ultrasonic signal relative to the surface echo of the reference composite material; and isolating a reference back-wall echo signal from the sample ultrasonic signal. A reference frequency spectrum of the reference back-wall ultrasonic signal is then determined. The invention further includes deriving the ultrasonic attenuation of the sample ultrasonic signal as the ratio of the sample frequency spectrum to the reference frequency spectrum over a predetermined frequency range. Comparing the derived ultrasonic attenuation to predetermined attenuation standards permits evaluating the porosity of the sampled composite material.

19 Claims, 4 Drawing Sheets

U.S. PATENT DOCUMENTS

| | | | |
|---|---|---|---|
| 4,607,341 A | 8/1986 | Monchalin | 364/557 |
| 4,633,715 A | 1/1987 | Monchalin | 73/657 |
| 4,659,224 A | 4/1987 | Monchalin | 356/352 |
| 4,820,981 A | 4/1989 | Bussiere et al. | 324/222 |
| 4,854,173 A | 8/1989 | Mott et al. | 73/600 |
| 4,869,109 A | 9/1989 | Miglianico et al. | 73/602 |
| 4,941,474 A | 7/1990 | Pratt, Jr. | 128/660.01 |
| 4,966,459 A | 10/1990 | Monchalin | 356/358 |
| 5,062,296 A | 11/1991 | Migliori | 73/579 |
| 5,070,733 A | 12/1991 | Nagata et al. | 73/602 |
| 5,074,149 A | 12/1991 | Stearns | 73/579 |
| 5,080,491 A | 1/1992 | Monchalin et al. | 356/352 |
| 5,092,176 A | 3/1992 | Buttram et al. | 73/599 |
| 5,131,748 A | 7/1992 | Monchalin et al. | 356/352 |
| 5,137,361 A | 8/1992 | Heon et al. | 356/352 |
| 5,257,544 A | 11/1993 | Khuri-Yakub et al. | 73/579 |
| 5,351,543 A | 10/1994 | Migliori et al. | 73/579 |
| 5,402,235 A | 3/1995 | Monchalin | 356/357 |
| 5,406,850 A | 4/1995 | Bouchard et al. | 73/620 |
| 5,608,166 A | 3/1997 | Monchalin et al. | 73/657 |
| 5,852,243 A | 12/1998 | Chang et al. | 73/659 |
| 6,043,884 A | 3/2000 | Curbelo | 356/346 |
| 6,057,927 A | 5/2000 | Lévesque et al. | 356/432 T |
| 6,104,942 A | 8/2000 | Kruger | 600/407 |
| 6,292,682 B1 | 9/2001 | Kruger | 600/407 |

OTHER PUBLICATIONS

WO 98 22801; Jeffrey S. White, et al.; Physical Parameter Measuring Apparatus and Method Thereof.

R. Roderick and R. Truell, "The Measurement of Ultrasonic Attenuation in Solids by the Pulse Technique and Some Results in Steel", *Journal of Applied Physics*, 23 (7) pp. 267–279.

O.R. Gericke, "Ultrasonic Spectroscopy of Steel", Mater. Res. Stand., 5 (23), 1965.

D. Ackers, C. Vaccaro, S. Elssworth and D. Petit, "The Effect of Porosity Density and Configuration in Composite Materials on the Ultrasonic Waveform", in *Review of Progress in QNDE*, vol. 15, Edited by D. Thompson and D.E. Chimenti, Plenum Press, New York, pp. 1239–1249 (1995).

Pouet, B. , Rasolofosaon, N.J.P., "Ultrasonic Intrinsic Attenuation Measurement Using Laser Techniques", *Ultrasonics Symposium*, 1989, Proceedings, IEEE 1989, vol. 1, pp. 545–549 (1989).

J.D. Aussel and J.P. Monchalin, "Measurement of Ultrasound Attenuation by Laser–Ultrasonics", *Journal of Applied Physic*, 65 (8) pp. 2918–2922 (1989).

F.A. Reed, T.J., Batzinger, R.W. Reed and S. Jonsson, "Porosity Measurements in Composites Using Ultrasonice Attenuation Methods", in Review of Progress in QNDE, vol.12, Edited by D. Thompson and D.E. Chimenti, Plenum Press, New York, pp. 1265–1272 (1993).

SYSTEM AND METHOD OF DETERMINING POROSITY IN COMPOSITE MATERIALS USING ULTRASOUND

This application claims priority to U.S. Provisional Application Serial No. 60/218,341, filed Jul. 14, 2000 entitled "A SYSTEM AND METHOD FOR DETECTING POROSITY OF A COMPOSITE MATERIAL USING ULTRASONICS," and is incorporated herein by reference in its entirety.

Additionally, this application is related to and incorporates by reference U.S. Patent Application entitled "METHOD AND APPARATUS FOR ULTRASONIC LASER TESTING" filed on Jun. 30, 1999, which was accorded Ser. No. 09/343,920.

Additionally, this application is related to and incorporates by reference U.S. patent application Ser. No. 09/416,399, filed on Oct. 10, 1999, entitled "METHOD AND APPARATUS FOR DETECTING ULTRASONIC SURFACE DISPLACEMENTS USING POST-COLLECTION OPTICAL AMPLIFICATION" to Thomas E. Drake.

BACKGROUND OF THE INVENTION

TECHNICAL FIELD OF THE INVENTION

The present invention relates generally to an apparatus and method of non-destructive evaluation of materials, especially composite materials, and more particularly, to an apparatus and method for ultrasonically measuring the porosity of a composite material by accessing only one side of the composite material.

In recent years, the use of advanced composite structures has experienced tremendous growth in the aerospace, automotive, and many other commercial industries. While composite materials offer significant improvements in performance, they require strict quality control procedures in the manufacturing processes. Specifically, non-destructive evaluation ("NDE") methods are required to assess the structural integrity of composite structures; for example, to detect inclusions, delaminations and porosities. Conventional NDE methods, however, are very slow, labor-intensive, and costly. As a result, testing procedures adversely increase the manufacturing costs associated with composite structures.

Various methods and systems have been proposed to assess the structural integrity of composite structures. One method to generate and detect ultrasound using lasers is disclosed in U.S. Pat. No. 5,608,166, issued Mar. 4, 1997, to Monchalin et al. (the "'166 Patent"). The '166 Patent discloses the use of a first modulated, pulsed laser beam for generating ultrasound on a work piece and a second pulsed laser beam for detecting the ultrasound. Phase modulated light from the second laser beam is then demodulated to obtain a signal representative of the ultrasonic motion at the surface of the work piece. A disadvantage associated with this approach is that the first pulsed laser beam must be modulated.

Fiber-reinforced polymer-matrix composite materials have been proved of great interest in various fields for their high strength and low weight. In the aircraft industry in particular, the use of these materials increases steadily. However, polymer-matrix composites also must be inspected before installation for the presence of defects such as delaminations, inclusions, and porosity.

Porosity is the presence of voids created in composites during manufacturing. Measurement of ultrasonic attenuation provides a measurement of porosity level. Ultrasonic techniques were found to be the best technique to assess porosity level in composites. Unfortunately, it is not always possible to use a self-referencing technique exploiting two different echoes in the signal, like two back-wall echoes. This is because in some cases, the porosity is so high that barely one echo is observed. Porosity measurements must rely on only one echo. Therefore, unlike delamination and inclusions, the ultrasonic response to porosity is frequency and amplitude dependent. This characteristic means that each ultrasonic system has a different response to a given porosity level. Therefore, each ultrasonic system must be calibrated relative to certain porosity levels.

Figure 1:
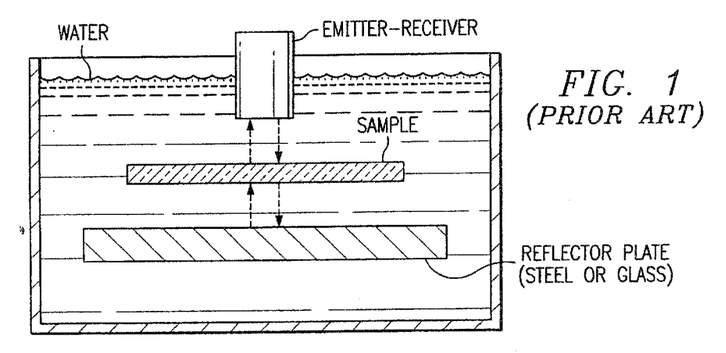
FIGS. 1 and 2 show prior art methods of evaluating porosity in composite materials.
Figure 2:
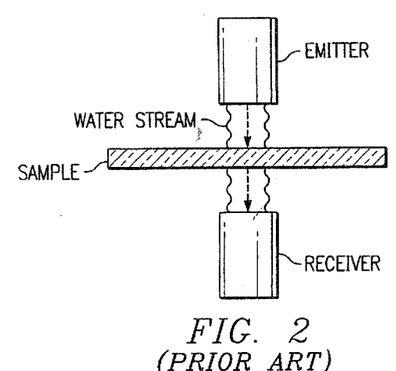

Two different techniques are used to measure porosity: reflected through transmission ultrasound (RTTU) and through transmission ultrasound (TTU). These methods compare the amplitude of an ultrasonic wave that has propagated through a sample with the amplitude of an ultrasonic wave that has propagated through a reference sample. The ultrasonic echo used is the one reflected from a steel or glass plate in the RTTU technique. FIG. 1 depicts this operation. Alternatively, in the TTU technique, ultrasonic echo is the echo coming directly from the piezoelectric emitter. FIG. 2 illustrates the TTU Technique Unfortunately, these techniques require an ultrasonic couplant, such as water and access to both sides of each composite panels. Ultrasonic refraction at the water/composite interface changes the ultrasonic wave direction when the piezoelectric emitter is not normal to the sample surface. Porosity must be evaluated at all points over the sample surface. The ultrasonic system must be moved at several positions over the sample surface to form a tight grid of ultrasonic measurements. The grid spacing must be smaller than the size of a critical porosity defect. The normalcy requirement makes the scanning of samples having curved surfaces expensive and slow. Moreover, when the two sides of a composite part are not accessible, such as for a closed box, porosity evaluations for such parts simply cannot be made using these techniques.

Therefore, a need has arisen for a method and system that permit making porosity measurements and evaluations of composite materials, which corrects the problems identified above, including the problems of needing water or similar couplant or access to both sides of the composite material.

Moreover, there is the need for a method and system that permit making porosity measurements and evaluations of composite materials without the need to modulate a pulsed laser beam or other similar problems such as those existing with the '166 Patent.

SUMMARY OF THE INVENTION

The present invention provides a method and system for ultrasonically measuring the porosity in a composite material by accessing only one side of the composite material that substantially eliminates or reduces disadvantages and problems associated with previously developed ultrasonic systems and methods.

The present invention provides a method and system to measure porosity in composite material by ultrasonic techniques, such as laser ultrasound, which method only requires access to one side of the composite material. The method and system evaluate ultrasonic attenuation that correlates with porosity, by comparing the amplitude of the sample material back-wall echo to the amplitude of the back-wall echo of a reference sample. The method and system further involves normalizing the signal amplitude according to a reference echo (for laser-ultrasound, the surface echo) to eliminate amplitude variations caused by phenomena not related to porosity.

According to another aspect of the invention, there is provided a method and system for ultrasonically measuring the porosity in a sample composite material by accessing only one side of the sample composite material. The method includes the steps of measuring a sample ultrasonic signal from the sample composite material, normalizing the sample ultrasonic signal relative to the surface echo of the sample composite material, and isolating a sample back-wall echo signal from the sample ultrasonic signal. A sample frequency spectrum of said sample back-wall ultrasonic signal is then determined. Next, the method and system include the steps of measuring a reference ultrasonic signal from a reference composite material, normalizing said reference ultrasonic signal relative to the surface echo of the reference composite material and isolating a reference back-wall echo signal from said sample ultrasonic signal. A reference frequency spectrum of said reference back-wall ultrasonic signal is then determined. The invention further includes deriving the ultrasonic attenuation of the sample ultrasonic signal as the ratio of the sample frequency spectrum to the reference frequency spectrum over a predetermined frequency range. Comparing the derived ultrasonic attenuation to predetermined attenuation standards permits evaluating the porosity of the sampled composite material.

A technical feature of the present invention is the use of the back-wall echo amplitude of a composite material and comparing it to the back-wall echo amplitude measured from a reference composite material. The present invention normalizes all ultrasonic signals (including reference sample echo) relative to a reference echo (in the case of laser-ultrasound, the surface echo) to eliminate amplitude variations caused by any effects not directly related to porosity Another technical feature of the present invention is the use of spatial averaging of the ultrasonic traces to easily identify the position of the back wall echo. The present invention includes calculating the full frequency spectra of the sample back wall echo and of the reference back wall echo using windowing techniques. The ratio of these two spectra provides the ultrasonic attenuation as a function of frequency. The present invention uses the ultrasonic attenuation at a given frequency to evaluate porosity relatively to standards established previously for the material inspected, or to use the frequency dependency of ultrasonic attenuation to correlate with porosity level.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE PREFERRED EMBODIMENT

Preferred embodiments of the present invention are illustrated in FIGS. 3 through 10 of the drawings, like numerals being used for like and corresponding parts of the various drawings.

Figure 3:
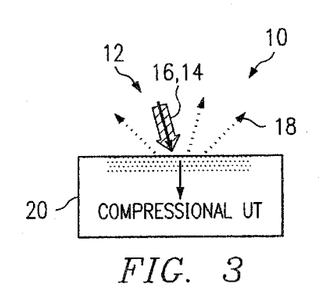
FIG. 3 illustrates the use of a generation laser beam and a detection laser beam coaxial therewith.

FIG. 3 illustrates ultrasonic configuration 10; including incoming laser beam 12 which represents a generation laser beam 14 and a coaxial detection laser beam 16 upon a remote target 20. Generation laser beam 14 causes thermoelastic expansion in the target 20 in the form of ultrasonic surface deformations, which deformations modulate, scatter and reflect detection laser beam 16, represented by the phase-modulated light 18 directed away from target 20.

Figure 4:
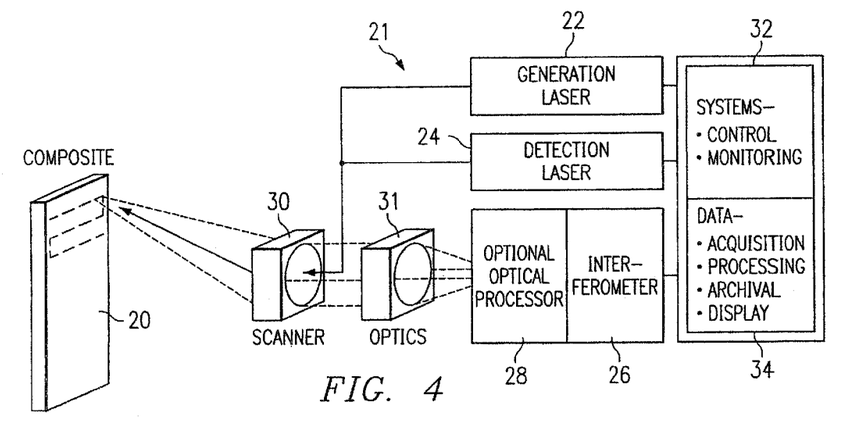
FIG. 4 is a block diagram showing the basic components of an apparatus for performing ultrasonic laser testing.

FIG. 4 illustrates in block diagram form the basic components of an apparatus 21 for performing ultrasonic laser testing. Apparatus 21 comprises a generation laser 22, a detection laser 24, an interferometer 230, an optional optical processor 235, an optical scanner 240, collection optics 31, systems controller 32, and data acquisition and processing apparatus 34. Generation laser 22 and detection laser 24 generate a generation laser beam 14 and a detection laser beam 16, respectively, which are directed by optical scanner 240 upon a target 20, which is typically a composite material. The generation laser 22 produces a compressional ultrasonic wave in the material normal to the surface of the target 20. The compressional ultrasonic wave is the result of thermoelastic expansion of the composite material as it absorbs generation laser beam 14.

The generation laser 22 must be of a frequency that is readily absorbed into the surface of target 20 without causing ablation or breaking down the target material, and it must be of the appropriate pulse duration to induce ultrasonic surface deformations. For example, a transverse-excited atmospheric ("TEA") $CO_2$ laser can be used to produce a 10.6-micron wavelength beam for a 100-nanosecond pulse. The power of the laser must be sufficient to deliver, for example, a 0.25-joule pulse to the target, which may require a 100-watt laser operating at a 400 Hz pulse repetition rate. The generation laser should be absorbed as heat into the target surface thereby causing thermoelastic expansion without ablation.

The detection laser 24 must be of sufficient pulse duration to not induce ultrasonic surface displacements. For example, a Nd:YAG laser can be used. The power of this laser must be sufficient to deliver, for example, a 100 millijoule, 100-microsecond pulse, which may require a one-kilowatt laser.

U.S. Pat. No. 6,122,060, entitled "METHOD AND APPARATUS FOR DETECTING ULTRASONIC SURFACE DISPLACEMENTS USING POST-COLLECTION OPTICAL AMPLIFICATION," issued to Thomas E. Drake, Jr. on Sep. 19, 2000 (the "Drake Patent") and to which the present invention claims priority in part further describes the above-illustrated system to include a detection laser to generate a first pulsed laser beam to detect the ultrasonic surface displacements on a surface of the target. Collection optics to collect phase modulated light from the first pulsed laser beam either reflected or scattered by the target. An optical amplifier which amplifies the phase modulated light collected by the collection optics. An interferometer which processes the phase modulated light and generates at least one output signal. A processor that processes the at least one output signal to obtain data representative of the ultrasonic surface displacements at the target. The present invention was developed for the effort relating to Drake and may be used in such an environment. Accordingly, the technical information described in Drake is hereby incorporated by reference.

Figure 5A:
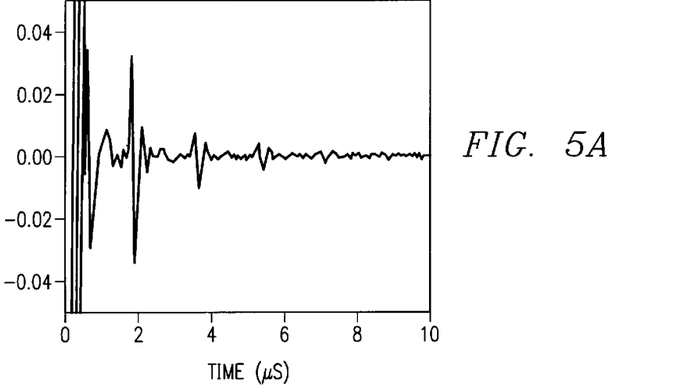
FIG. 5A and B shows an ultrasonic signal from a low porosity composite and an ultrasonic signal obtained from a medium-to-severe porosity composite.
Figure 5B:
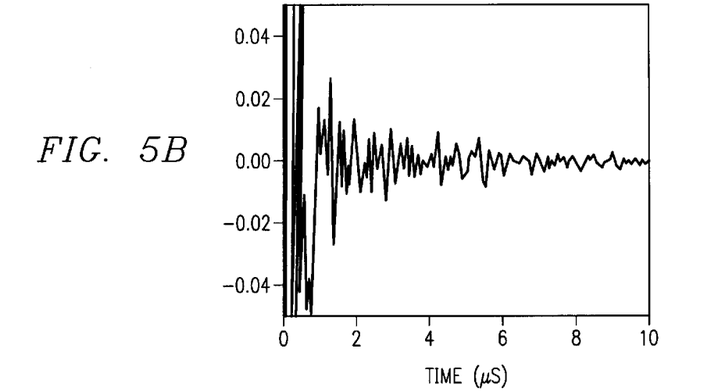

The present invention measures the ultrasonic attenuation using only a back-wall echo to evaluate porosity in composite parts. This procedure is useful for ultrasonic techniques requiring access to only one side of the sample. The first step is to acquire the ultrasonic signal. FIGS. 5A and 5B presents ultrasonic signals obtained using laser-ultrasound in a composite with low porosity, in FIG. 5A, and in a composite with medium to severe porosity, in FIG. 5B.

Certain aspects of ultrasonic attenuation measurement are well-known techniques for porosity evaluation. Ultrasonic evaluation of attenuation and, using ultrasonic attenuation for solid-state material characterization, are understood, as is the idea of using the ratio of frequency spectra to calculate attenuation as a function of frequency is well known in the art. Known techniques measure small ultrasonic attenuation variations. These measurements are performed from only one side of the sample, but water coupling is required and samples must have polished surfaces. In most cases of using ultrasonic attenuation to evaluate porosity, either TTU technique or RTTU technique is used. Both approaches use the ratio of two back wall echoes to evaluate attenuation.

Figure 6:
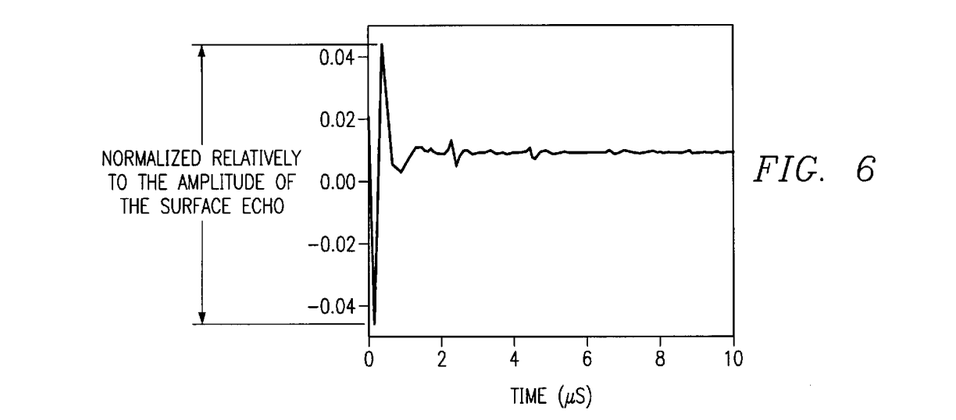
FIG. 6 shows an example of laser-ultrasound signal normalization using the surface echo.

FIGS. 5A and 5B show ultrasonic signals from a low porosity composite, in FIG. 5A, and ultrasonic signal obtained from a medium-to-severe porosity composite in FIG. 5B. One difficulty with the use of a single back-wall echo is that if the amplitude of the measured signal is affected by another factor than porosity, porosity measurement can produce a false reading. The ultrasonic signals need to be normalized in some manner. For this purpose, an ultrasonic signal that is not affected by porosity can be used. In the case of laser-ultrasound, this echo is called surface echo. This echo is produced by the surface displacement created by thermal expansion. The surface echo does not result from an ultrasonic wave. It is directly proportional to the quantity of light collected by the detection system and to the efficiency of the generation mechanism, assuming laser-ultrasound generation in an homogeneous material and a flat-frequency response of the detection system. Even if these conditions are not perfectly matched, normalization by the surface provides in a first approximation a good correction for variations of reflectivity and of generation and for variations of measurement incidence angle. FIG. 6 shows an example of laser-ultrasound signal normalization using the surface echo.

The next step in the process of the present invention is to identify the arrival time of the back-wall echo. In FIG. 5A, the first back-wall echo is easily identified. In the case of FIG. 5B, on the other hand, the identification of the back-wall echo is not easy. To identify the exact time of the back-wall echo, the ultrasonic signals can be spatial averaged to eliminate the spurious echoes caused by backscattering on porosity defects. The spatially-averaged signal at a given position is obtained by averaging the values of the signals at neighbor positions for each time. For example, the spatial-averaged signal at position (50,50) is obtained by averaging for each time values the ultrasonic signals between position (48,48) and (52,54) if a kernel of 5×5 is used. The spatial averaging is used only to identify the time of the back-wall echo. The back-wall echo arrival time of the spatial-averaged signal is used on the non-averaged signal to window correctly the back-wall echo in case sample thickness varies.

Figure 7A:
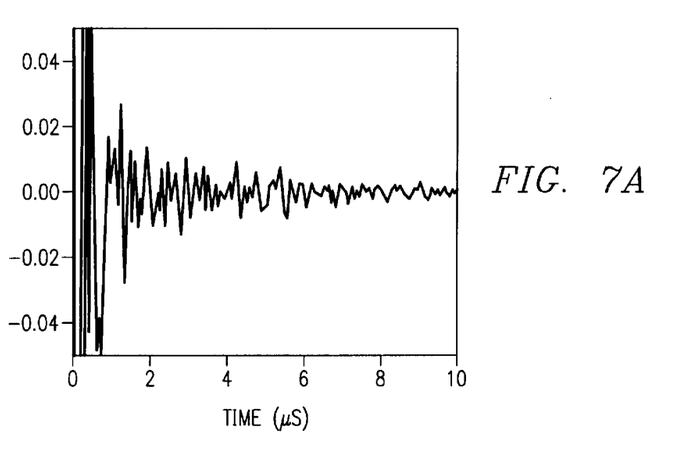
FIG. 7 presents the result of spatial averaging to identify the arrival time of a back-wall echo in a medium-to-severe porosity composite.
Figure 7B:
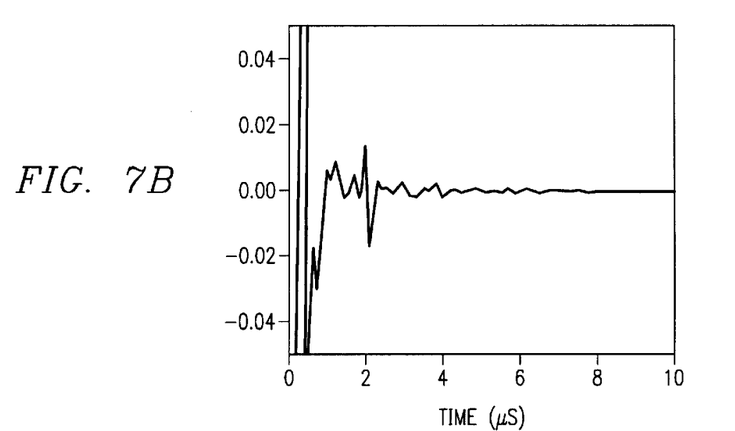
Figure 8:
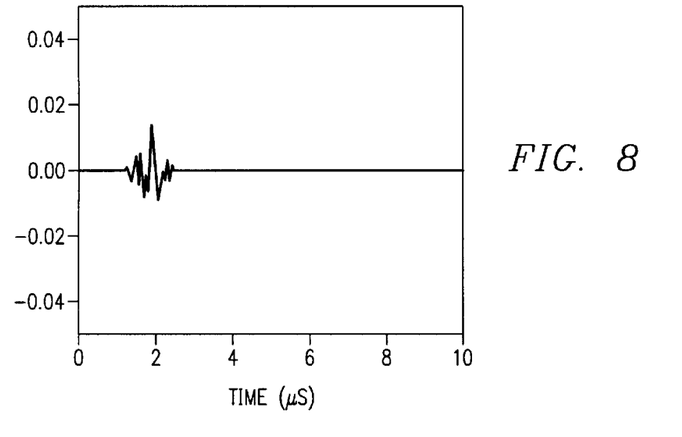
FIG. 8 presents the isolation of the back-wall echo for a composite material according to the present invention.

FIGS. 7A and 7B present the result of spatially averaging to identify the arrival time of a back-wall echo in a medium-to-severe porosity composite. In particular, FIG. 7A shows the ultrasonic signal without spatial averaging, while FIG. 7B depicts the ultrasonic signal at the same position using spatial averaging with a 9×9 kernel. When the arrival time of the back-wall echo has been found. This echo must be isolated from the remaining of the signal. The echo is isolated using windowing techniques. Different types of windowing techniques may be used, according to the given material and the type of signal received FIG. 8 presents the isolation of the back-wall echo of FIG. 7A. The window position was obtained using the maximum of the analytic signal of FIG. 7B inside a time-window determined so that the surface echo does not interfere. In particular, FIG. 8 shows the effect of isolating back-wall echo from the rest of the signal using classical windowing techniques. The frequency spectrum of the back-wall echo is then calculated. This frequency spectrum is then divided by the frequency spectrum of a reference signal. The reference signal is obtained using the same experimental procedure and the same signal-processing steps as the ones described previously for the signal currently analyzed. The reference signal is obtained from a pristine sample made of the same material with very low porosity and having the same thickness than the sample currently tested.

Figure 9:
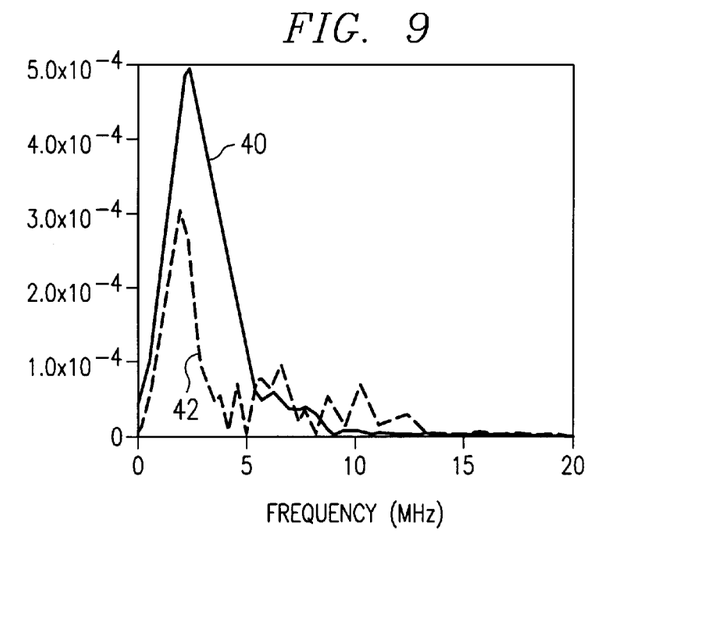
FIG. 9 presents the frequency spectra of a reference back-wall echo and of the sample back-wall echo of FIG. 8.

FIG. 9 presents the frequency spectra of a reference echo and of the back-wall echo of FIG. 8. In FIG. 9, the frequency spectra of a reference echo is shown as solid line 40 and of the echo of FIG. 6 is shown as dotted line 42. The ratio of the two spectra gives the ultrasonic attenuation as a function of frequency. To evaluate porosity, the ultrasonic attenuation at a given frequency can be compared to predetermined standards or the frequency dependency of attenuation can be used.

Figure 10:
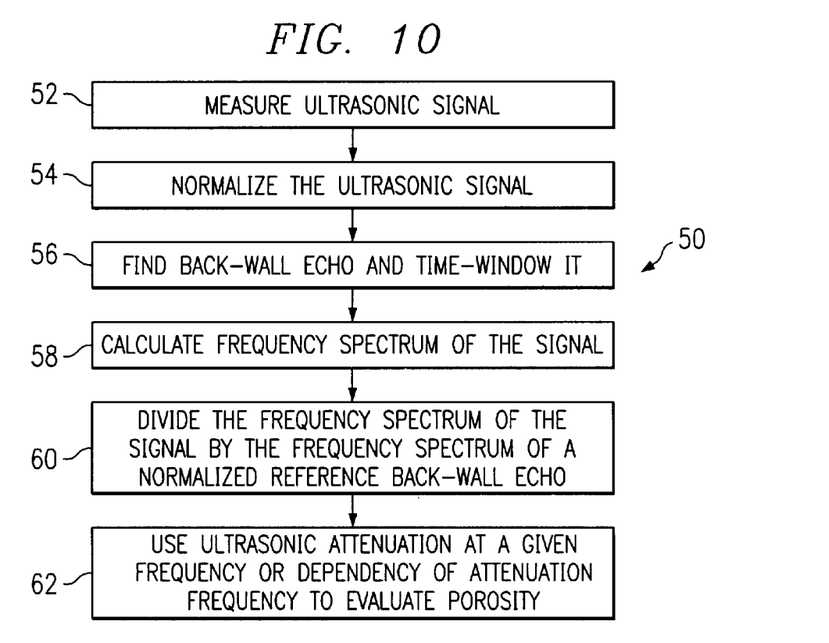
FIG. 10 shows the steps for performing ultrasonic attenuation measurements for porosity measurements according to one embodiment of the present invention.

FIG. 10 shows the steps required to perform ultrasonic attenuation measurements for porosity measurements according to the present invention. FIG. 10 shows flow diagram 50 of the process of the present invention for evaluating the porosity of a composite material. Referring to block 52, the present invention involves the step of measuring the ultrasonic signal from a composite material. This is done for both a reference composite material and a sample composite material. Then, the present invention involves normalizing each of these signal measurements, at block 54, with reference to amplitude of the respective materials' surface echoes. Block 56 references the steps of determining the back-wall echoes for both the normalized ultrasonic signals. Then, at block 58, the process continues through the steps of calculating the frequency spectrum of each of the normalized and measured signals. Block 60 accounts for the process step of dividing the frequency spectrum of the signal by the frequency spectrum of the normalized reference back-wall echo. This results in an ultrasonic attenuation measurement arising at a given frequency or dependency of attenuation frequency to evaluate the sample composite material's porosity, as block 62 depicts.

The process of FIG. 10 may be performed manually or automatically through a computer and related ultrasonic sensing system, such as the system described in FIGS. 1 and 2 and in the Drake Patent. Accordingly, the present invention encompasses a system fully capable of automatically performing instructions and possessing the necessary data storage and manipulation capabilities to carry out the described process.

Although the present invention has been described in detail, it should be understood that various changes, substitutions and alterations can be made hereto without departing from the spirit and scope of the invention as defined by the appended claims.

What is claimed is:

1. A method for ultrasonically measuring the porosity in a sample composite material by accessing only one side of the sample composite material, comprising the steps of:

measuring a sample ultrasonic signal from the sample composite material;

normalizing said sample ultrasonic signal;

isolating a sample back-wall echo signal from said sample ultrasonic signal;

determining a sample frequency spectrum of said sample back-wall ultrasonic signal;

measuring a reference ultrasonic signal from a reference composite material;

normalizing said reference ultrasonic signal;

isolating a reference back-wall echo signal from said sample ultrasonic signal;

determining a reference frequency spectrum of said reference back-wall ultrasonic signal;

deriving the ultrasonic attenuation of said sample ultrasonic signal as the ratio of said sample frequency spectrum to said reference frequency spectrum over a predetermined frequency range; and comparing said derived ultrasonic attenuation to predetermined standards for evaluating the porosity of the sampled composite material.

2. The method of claim 1, further comprising the step of generating said sample ultrasonic signal using a laser ultrasonic signal generating mechanism.

3. The method of claim 1, further comprising the step of spatially averaging said sample ultrasonic signal for identifying the arrival time of back-wall echo in a medium-to-severe porosity composite.

4. The method of claim 1, further comprising the step of isolating said sample back-wall echo signal using a windowing process.

5. The method of claim 1, further comprising the step of evaluating the porosity of said sample composite material predetermined frequencies relative to pre-determined frequency dependency standards.

6. The method of claim 1, further comprising the step of normalizing said sample ultrasonic signal relative to the surface echo of the sample composite material.

7. The method of claim 1, further comprising the step of generating said sample ultrasonic signal as a laser ultrasonic signal through the collection of phase modulated light from a first pulsed laser beam either reflected or scattered by the sample composite material and further amplifying the phase modulated light collected by the collection optics using an optical amplifier.

8. A system for ultrasonically measuring the porosity in a sample composite material by accessing only one side of the sample composite material, comprising:

an ultrasonic laser detection system to generate and measure a sample ultrasonic signal from the sample composite material;

a processor which:
      normalizes said sample ultrasonic signal relative to a surface echo of the sample composite material;
      isolates a sample back-wall echo signal from said sample ultrasonic signal;
      determines a sample frequency spectrum of said sample back-wall ultrasonic signal;
      normalizes a reference ultrasonic signal relative to a surface echo of a reference composite material;
      isolates a reference back-wall echo signal from the sample ultrasonic signal;
      determines a reference frequency spectrum of said reference back-wall ultrasonic signal;
      derives the ultrasonic attenuation of the sample ultrasonic signal as the ratio of the sample frequency spectrum to the reference frequency spectrum over a predetermined frequency range; and
      compares said derived ultrasonic attenuation to predetermined attenuation standards to for evaluating the porosity of the sampled composite material.

9. The system of claim 8, wherein the processor further spatially averages the sample ultrasonic signal to identify the arrival time of a back-wall echo in a medium-to-severe porosity composite.

10. The system of claim 8, wherein the processor further isolates the sample back-wall echo signal using a windowing process.

11. The system of claim 8, wherein the processor further evaluates the porosity of the sample composite material predetermined frequencies relative to pre-determined frequency dependency standards.

12. The system of claim 8, wherein the processor further normalizes the sample ultrasonic signal relative to the surface echo of the sample composite material.

13. The system of claim 8, wherein the processor further generates the sample ultrasonic signal as a laser ultrasonic signal through the collection of phase modulated light from a first pulsed laser beam either reflected or scattered by the sample composite material and further amplifying the phase modulated light collected by the collection optics using an optical amplifier.

14. A method for detecting ultrasonic surface displacements on a target including method for ultrasonically measuring the porosity in a sample composite material by accessing only one side of the sample composite material, comprising the steps of:

generating ultrasonic surface displacements at the target;

using a first pulsed laser beam to detect the ultrasonic surface displacements at the target;

collecting phase modulated light from the first pulsed laser beam scattered by the target;

optically amplifying the phase modulated light after the phase modulated light has been collected;

preventing reflected phase modulated light feedback into an optical amplifier with at least one optical isolation assembly placed in the path of propagation of the phase modulated light which has been collected;

processing the phase modulated light to obtain data representative of the ultrasonic surface displacements at the target; and ultrasonically measuring the porosity in a sample composite material by accessing only one side of the sample composite material, wherein the step of ultrasonically measuring further comprising the steps of:

measuring a sample ultrasonic signal from the sample composite material;

normalizing the sample ultrasonic signal relative to the surface echo of the sample composite material;

isolating a sample back-wall echo signal from the sample ultrasonic signal;

determining a sample frequency spectrum of the sample back-wall ultrasonic signal;

measuring a reference ultrasonic signal from a reference composite material;

normalizing the reference ultrasonic signal relative to the surface echo of the reference composite material;

isolating a reference back-wall echo signal from the sample ultrasonic signal;

determining a reference frequency spectrum of the reference back-wall ultrasonic signal;

deriving the ultrasonic attenuation of the sample ultrasonic signal as the ratio of the sample frequency spectrum to the reference frequency spectrum over a predetermined frequency range; and comparing the derived ultrasonic attenuation to predetermined attenuation standards to for evaluating the porosity of the sampled composite material.

15. The method of claim 14, further comprising the step of generating the sample ultrasonic signal using a laser ultrasonic signal generating mechanism.

16. The method of claim 14, further comprising the step of spatially averaging the sample ultrasonic signal for identifying the arrival time of a back-wall echo in a medium-to-severe porosity composite.

17. The method of claim 14, further comprising the step of isolating the sample back-wall echo signal using a windowing process.

18. The method of claim 14, further comprising the step of evaluating the porosity of the sample composite material predetermined frequencies relative to pre-determined frequency dependency standards.

19. The method of claim 14, further comprising the step of normalizing the sample ultrasonic signal relative to the surface echo of the sample composite material.

* * * * *